(12) United States Patent
Bochkariov

(10) Patent No.: US 6,475,440 B1
(45) Date of Patent: Nov. 5, 2002

(54) APPLICATOR FOR USE IN DEPOSITION OF FLUID SAMPLES ONTO A SUBSTRATE SURFACE

(75) Inventor: Dmitry Bochkariov, Mountain View, CA (US)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

(21) Appl. No.: 09/382,567

(22) Filed: Aug. 25, 1999

Related U.S. Application Data

(60) Provisional application No. 60/100,554, filed on Sep. 16, 1998.

(51) Int. Cl.[7] .............................. B01L 3/02; B01L 3/00; C12M 1/26; C12M 3/00; G01N 1/00; G01N 1/10; G01N 1/12; B43K 5/00
(52) U.S. Cl. ...................... 422/100; 422/99; 436/180; 436/174; 73/864.72; 435/309.1; 401/221
(58) Field of Search .................. 422/100, 99; 436/180, 436/174; 435/309.1, 309.3; 73/864.72; 401/221, 287

(56) References Cited

U.S. PATENT DOCUMENTS

| | | | | |
|---|---|---|---|---|
| 135,080 A | * | 1/1873 | Chinn | 401/221 |
| 435,969 A | * | 9/1890 | Heinz | 401/221 |
| 545,140 A | * | 8/1895 | Stege | 401/287 |
| 576,150 A | * | 2/1897 | Rathbun | 401/221 |
| 594,284 A | * | 11/1897 | Renz | 401/221 |
| 677,008 A | * | 6/1901 | Winton | 401/221 |
| 1,189,331 A | * | 7/1916 | Worth | 401/221 |
| 2,432,012 A | * | 12/1947 | Hanle | 401/221 |
| 2,497,249 A | * | 2/1950 | Weston | 401/221 |
| 2,979,030 A | * | 4/1961 | Harrington | 401/221 |
| 4,298,345 A | * | 11/1981 | Sodickson et al. | 23/230 R |
| 4,589,791 A | * | 5/1986 | Weihrauch | 401/287 |
| 4,865,482 A | * | 9/1989 | Van Landingham | 401/287 |
| 4,971,763 A | * | 11/1990 | Columbus | 422/100 |
| 5,242,974 A | | 9/1993 | Holmes | 525/54.11 |
| 5,336,468 A | * | 8/1994 | Tezuka et al. | 422/100 |
| 5,384,261 A | | 1/1995 | Winkler et al. | 436/518 |
| 5,405,783 A | | 4/1995 | Pirrung et al. | 436/518 |
| 5,412,087 A | | 5/1995 | McGall et al. | 536/24.3 |
| 5,424,186 A | | 6/1995 | Fodor et al. | 435/6 |
| 5,429,807 A | | 7/1995 | Matson et al. | 422/131 |
| 5,436,327 A | | 7/1995 | Southern et al. | 536/25.34 |
| 5,445,934 A | | 8/1995 | Fodor et al. | 435/6 |
| 5,472,672 A | | 12/1995 | Brennan | 422/131 |
| 5,527,681 A | | 6/1996 | Holmes | 435/6 |
| 5,529,756 A | | 6/1996 | Brennan | 422/131 |
| 5,545,531 A | | 8/1996 | Rava et al. | 435/6 |

(List continued on next page.)

FOREIGN PATENT DOCUMENTS

| | | |
|---|---|---|
| EP | 0 742 287 A2 | 11/1996 |
| EP | 0 799 897 A1 | 10/1997 |
| WO | 93/17126 | 9/1993 |
| WO | 95/11995 | 5/1995 |
| WO | 95/35505 | 12/1995 |

*Primary Examiner*—Lyle A. Alexander
*Assistant Examiner*—Brian R. Gordon
(74) *Attorney, Agent, or Firm*—Bret E. Field; Bozicevic, Field & Francis

(57) ABSTRACT

Applicator devices for depositing a fluid sample onto a substrate, as well as methods for their use, are provided. The subject devices are elongate in shape and have a first end and a second end. The first end has a planar surface of substantially circular shape with a conical protuberance arising therefrom. The second end may have a means for attaching to an automated movement means. In using the subject devices, the first end is dipped into a fluid sample and then contacted with the surface of a substrate in a manner sufficient to deposit a fluid sample onto the substrate surface. The subject devices and methods find use in a variety of different applications, particularly in the preparation of biopolymeric arrays.

14 Claims, 4 Drawing Sheets

U.S. PATENT DOCUMENTS

| | | |
|---|---|---|
| 5,554,501 A | 9/1996 | Coassin et al. .................. 435/6 |
| 5,556,752 A | 9/1996 | Lockhart et al. ................ 435/6 |
| 5,561,071 A | 10/1996 | Hollenberg et al. ............. 437/1 |
| 5,624,711 A | 4/1997 | Sundberg et al. ............ 427/261 |
| 5,639,603 A | 6/1997 | Dower et al. ................... 435/6 |
| 5,658,734 A | 8/1997 | Brock et al. .................... 435/6 |
| 5,756,050 A * | 5/1998 | Ershow et al. |
| 5,962,329 A * | 10/1999 | Ershov et al. ................. 436/50 |
| 6,066,297 A * | 5/2000 | Torti et al. .................... 422/100 |
| 6,143,572 A * | 11/2000 | Grand et al. ................... 436/80 |
| 6,197,259 B1 * | 3/2001 | Kelly et al. .................. 422/100 |
| 6,255,119 B1 * | 7/2001 | Baier .......................... 436/180 |

* cited by examiner

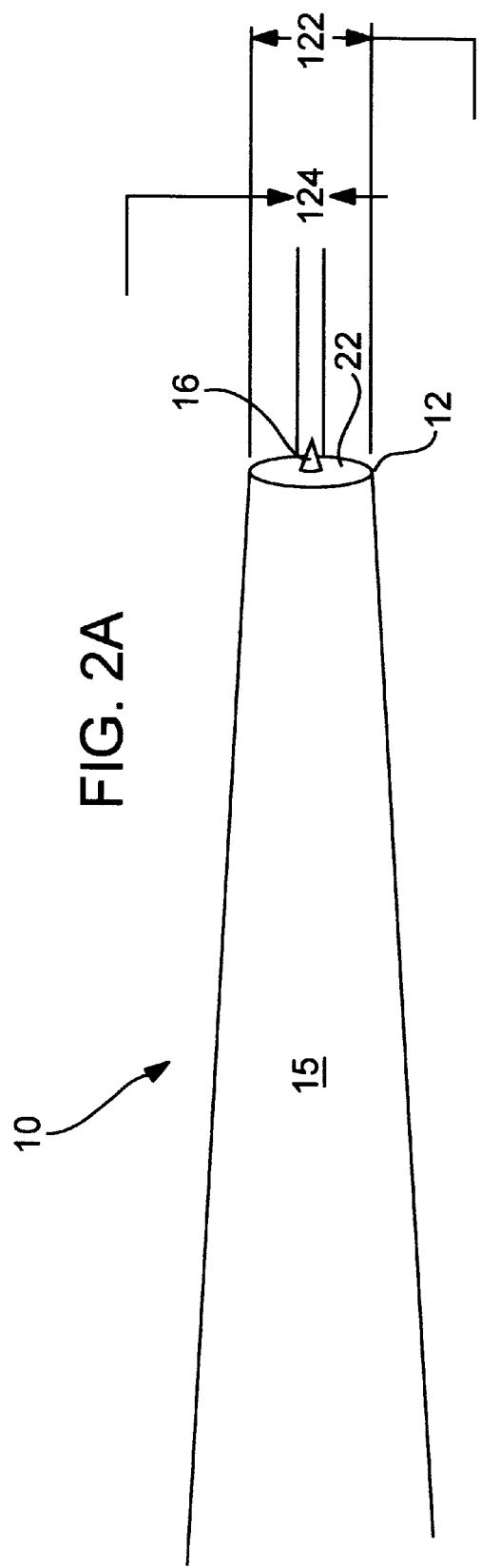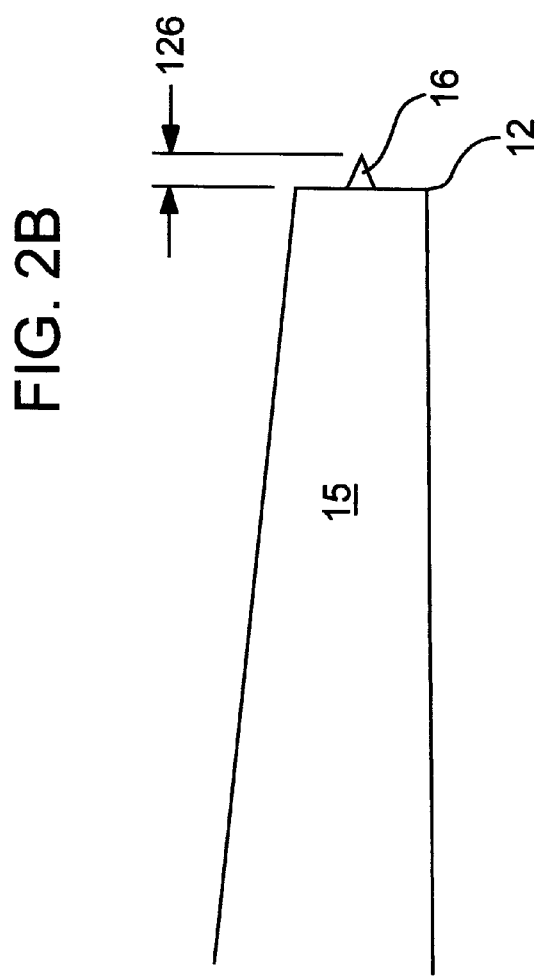

FIG. 4A
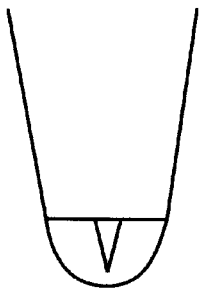
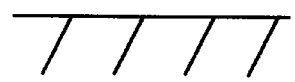
FIG. 4B
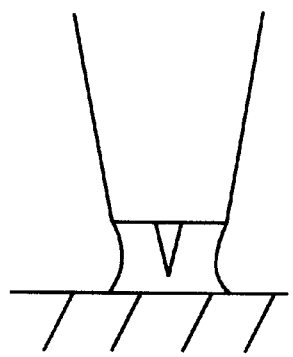
FIG. 4C
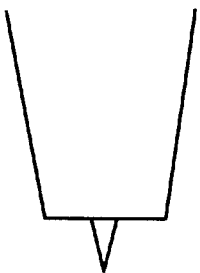
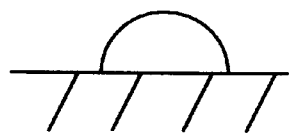

APPLICATOR FOR USE IN DEPOSITION OF FLUID SAMPLES ONTO A SUBSTRATE SURFACE

CROSS REFERENCE TO RELATED APPLICATIONS

Pursuant to 35 U.S.C. § 119 (e), this application claims priority to the filing date of the United States Provisional Patent Application Serial No. 60/100,554 filed on Sep. 16, 1998, the disclosure of which is herein incorporated by reference.

INTRODUCTION

1. Technical Field

The field of this invention is biopolymeric arrays.

2. Background of the Invention

"Biochips" or arrays of binding agents, such as oligonucleotides and peptides, have become an increasingly important tool in the biotechnology industry and related fields. These binding agent arrays, in which a plurality of binding agents are deposited onto a solid support surface in the form of an array or pattern, find use in a variety of applications, including gene expression analysis, drug screening, nucleic acid sequencing, mutation analysis, and the like.

Such arrays may be prepared in a number of different ways. For example, DNA arrays may be prepared manually by spotting DNA onto the surface of a substrate with a micro pipette. See Khrapko et al., DNA Sequence (1991) 1:375–388. Alternatively, the dot-blot approach, as well as the derivative slot-blot approach, may be employed in which vacuum manifold transfers aqueous DNA samples from a plurality of wells to a substrate surface.

In yet another method of producing arrays of biopolymeric molecules, a pin is dipped into a fluid sample and then contacted with the substrate surface. By using a plurality or array of pins, one can transfer a plurality of samples to the substrate surface at the same time. Although such methods are efficient, they are not completely satisfactory. For example, depending the particular technique used to deposit the fluid sample, e.g. when the pin is contacted with the substrate surface, one can obtain spots of deposited fluid that have an irregular shape, spots that have a doughnut shape, or other undesirable configurations. Further disadvantages may include a lack of reproducibility.

Alternatively, an array of capillaries can be used to produce biopolymeric arrays. See WO 95/35505. Although the use of capillaries has certain advantages over other methods, problems with spot doughnut-like shape and spot homogeneity or spot reproducibility may be encountered. Specifically, present methods may result in the production of a spot with a doughnut-like shape.

In yet another method of producing biopolymeric arrays, arrays of biopolymeric agents are "grown" on the surface of a substrate in discreet regions. See e.g. U.S. Pat. No. 5,143,854 and Fodor et al., Science (1991) 251:767–773. While effective in producing arrays, such methods are complicated as a plurality of synthesis steps are required. Furthermore, the achievable length of the grown biopolymer agent is limited.

Accordingly, there is continued interest in new methods of producing biopolymeric arrays, as well as devices for use therein. Ideally, such new methods and devices should produce arrays in which the biopolymeric spots have a substantially uniform and reproducible configuration. Furthermore, the methods should be simple, require few distinct steps and be adaptable to an automated format.

Relevant Literature

Patents and patent applications describing arrays of biopolymeric compounds and methods for their fabrication include: 5,242,974; 5,384,261; 5,405,783; 5,412,087; 5,429, 807; 5,436,327; 5,445,934; 5,472,672; 5,527,681; 5,529, 756; 5,545,531; 5,554,501; 5,556,752; 5,561,071; 5,599, 895; 5,624,711; 5,639,603; 5,658,734; WO 93/17126; WO 95/11995; WO 95/35505; EP 742 287; and EP 799 897.

Other references of interest include: Lockhart et al., Nature Biotechnology (1996) 14: 1675–1680; Shena et al., Science (1995) 270: 467–470; Schena et al., Proc. Nat'l Acad. Sci. USA (1996)93:10614–10619; Shalon et al., Genome Res. (1996) 6: 639–645; Milosavljevic et al., Genome Res. (1996) 6:132–141; Nguyen et al., Genomics (1995)29: 207–216; Piètu et al., Genome Res. (1996) 6: 492–503; Zhao et al., Gene (1995) 166:207213; Chalifour et al., Anal. Biochem. (1994) 216:299–304; Heller et al., Proc. Nat'l Acad. Sci. USA (1997) 94: 2150–2155; Khrapko et al., DNA Sequence (1991) 1:375–388; Lehrach et al., Hybridization Fingerprinting in Genome Mapping and Sequencing, Genome Analysis, Vol. 1 (Davies & Tilgham, eds)(Cold Spring Harbor Press) (1990) pp 39–81; and Schena, M., BioAssays (1996) 18: 427–431.

SUMMARY OF THE INVENTION

Applicator devices for depositing a fluid sample on the surface of a substrate, as well as methods for their use, are provided. The subject applicator devices are elongate in shape and have a first end and a second end. The first end is substantially planar with a circular shape. Arising from the surface of the first end is a conical protuberance. The second end of the elongate device may have a means for attaching to an automated movement means. In using the subject devices, the first end is introduced into a fluid sample and then contacted with a substrate surface, whereby a volume of the fluid sample is deposited on the substrate surface. The subject devices and methods find use in a variety of applications, particularly in the preparation of biopolymeric arrays, such as nucleic acid and protein arrays.

BRIEF DESCRIPTION OF THE FIGURES

FIGS. 2A and 2B provide a close up views of the first end of an applicator device according to the subject invention.

FIGS. 4A to 4C show an applicator according to the subject invention depositing fluid on a substrate surface.

DEFINITIONS

Figure 1:
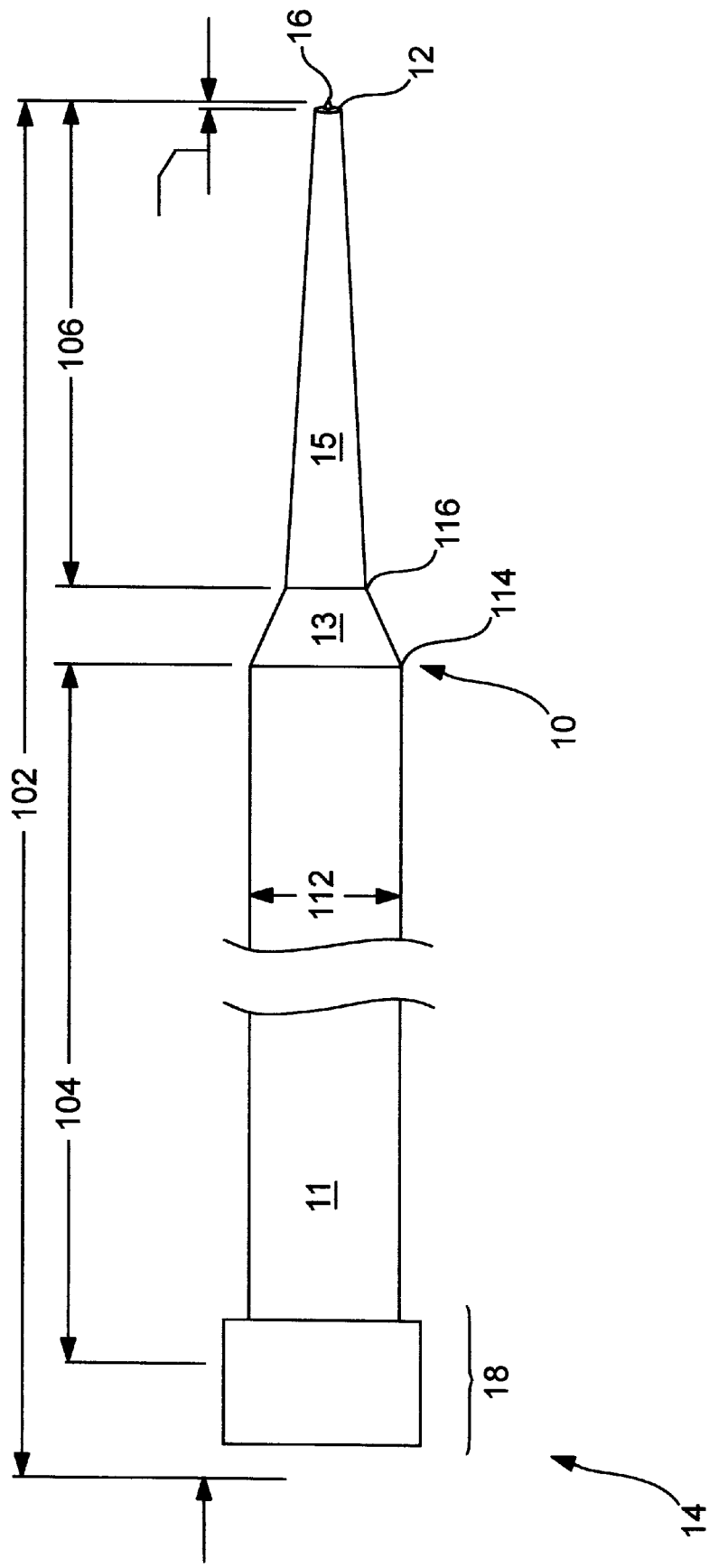
FIG. 1 provides a two-dimensional representation of an applicator device according o the subject invention.

The term "biopolymer" means any molecule that is composed of two or more monomeric units, where at least the monomeric units are naturally occurring or synthetic derivatives of naturally occurring monomeric units. As such, biopolymers include peptides and nucleic acids, both naturally occurring and non-naturally occurring, e.g. produced through genetic recombination techniques.

The term "peptide" as used herein refers to any compound produced by amide formation between a carboxyl group of one amino acid and an amino group of another amino acid.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g. deoxyribonucleotides or ribonucleotides.

The terms "ribonucleic acid" and "RNA" as used herein means a polymer composed of ribonucleotides.

The terms "deoxyribonucleic acid" and "DNA" as used herein means a polymer composed of deoxyribonucleotides.

The term "oligonucleotide" as used herein denotes single stranded nucleotide of from about 10 to 100 nucleotides and up to 200 nucleotides in length.

The term "polynucleotide" as used herein refers to single or double stranded polymer composed of nucleotide monomers of generally greater than 100 nucleotides in length.

DESCRIPTION OF THE SPECIFIC EMBODIMENTS

Applicator devices for use in the preparation of biopolymeric arrays, as well as methods for their use, are provided. The subject applicator devices are elongate in shape and have a first end and a second end. The first end has a substantially planar surface that is usually in circular shape. Arising from the planar surface of the first end is a conical protuberance. The second end of the subject devices may have a means for attaching to an automated movement means. To use the subject devices, the first end is dipped into a fluid sample and then contacted with a substrate surface in manner sufficient to deposit a volume of the fluid sample onto the surface. The subject applicator devices and methods find use in a variety of applications, particularly in the production of biopolymeric arrays. In further describing the subject invention, the applicator devices will be described in greater detail followed by a discussion of methods for their use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

THE APPLICATOR DEVICE

The applicator devices of the subject arrays are elongate in shape. By elongate in shape is meant that the overall length of the device is several times longer than the largest width dimension of the device, generally at least about 5 to 30 times longer, usually at least about 7 to 25 times longer, and more usually at least about 10 to 20 times longer. The applicator devices have a first end and a second end. The first end has a substantially planar surface with a conical protuberance arising therefrom. The dimensions of the first end, including the planar surface and the conical protuberance, are sufficient to be able to deposit a substantially circular fluid spot on the surface of a substrate, where the deposited spot is characterized by having a regular shape and substantially no voids or areas of little or no deposited fluid, e.g. as found in a doughnut shaped spot. The dimensions of the first end are also such that the applicator is capable of depositing spots on the surface in a reproducible fashion, such that there is substantially no variance between different spots deposited by the applicator, where by substantially no variance is meant that the surface area of any two spots deposited by the applicator under the same conditions will vary by less than about 30%, usually by less than about 20% and more usually by less than about 10%.

Figure 3:
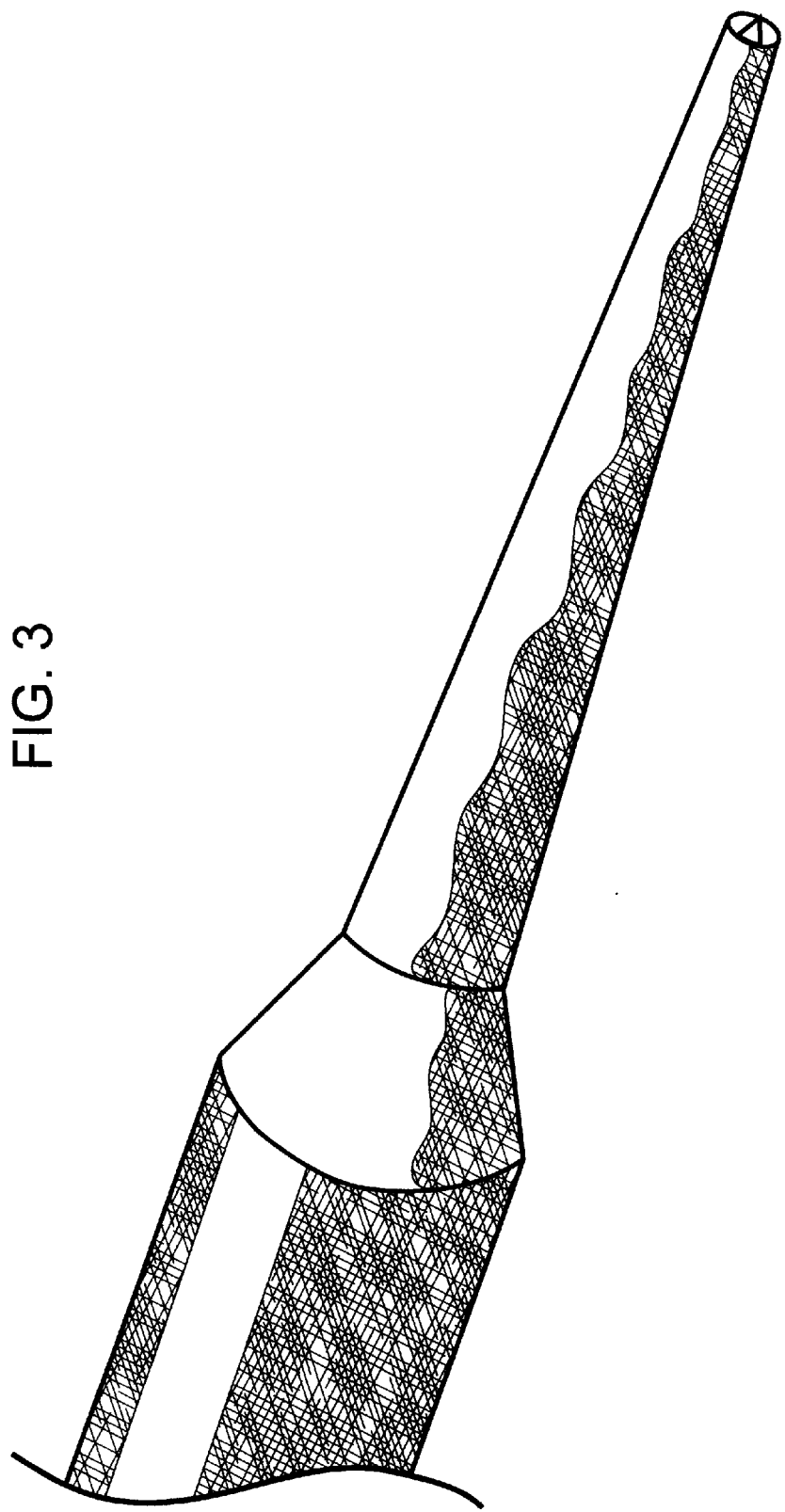
FIG. 3 provides a three-dimensional representation of an applicator device according to the subject invention.

The subject applicator devices will now be described in greater detail in terms of the figures. FIG. 1 provides a general two-dimensional representation of a device according to the subject invention. In FIG. 1, elongate device 10 has a first end 12 and a second end 14 separated by three regions, 11, 13 & 15, of different dimension. At first end 12 is conical protuberance 16. The purpose of the protuberance 16 is to prevent the larger surface of the first end 12 of the applicator from making contact with the surface onto which probes are being deposited during use. Thus, the spacial size of direct contact of the applicator with surface is minimized by the protuberance. The area of the extreme tip of protuberance 16 is kept at a minimum, where the tip area will not exceed about 10%, usually will not exceed about 5% and more usually will not exceed about 2% of the area of first end 12. In FIG. 3, a three-dimensional view of applicator device 10 is provided. dimensions of the device may vary. Turning back to FIG. 1, the overall length of the device will vary depending on the particular application in which the device is used. For the production of the biopolymeric arrays, the overall length, 102, of the device may range from about 10 to 100 mm, usually from about 15 to 80 mm and more usually from about 20 to 60 mm.

As shown in FIG. 1, the first and second ends of the device are separated by three different regions, 11, 13 & 15. The first of these regions may have any convenient configuration but will generally have a shape in which the cross-sectional area is constant along the entire length of the region. As such, the cross-sectional shape of region 11 may be square, elliptoid, triangular, circular, pentagonal or even irregular. In a preferred embodiment, the cross-section shape of region 11 will be circular such that the region has an overall tubular shape. As the cross-sectional area of region 11 is constant along the entire length of this region, the cross-sectional area at any two points of region 11 will be the same. The length of region 11 will vary greatly, but in devices for use in the production of biopolymeric arrays, the length 104 will generally range from about 5 to 80 mm, usually from about 10 to 60 mm and more usually from about 15 to 50 mm. The width of the device along region 11, as represented by 112, generally ranges from about 0.5 to 4.0 mm, usually from about 1.0 to 3.0 mm and more usually from about 1.5 to 2.5 mm.

Adjacent to first region 11 may be a second region 13. Second region 13 may be absent. However, when present second region 13 is typically shorter than first region 11, usually at least about 4 fold shorter, and more usually at least about 10 fold shorter. As such, the length of second region 13 generally ranges from about 0.8 mm to 6.0 mm, usually from about 1.0 mm to 5.0 mm and more usually from about 1.25 mm to 2.0 mm. In most embodiments, the width of second region 13 at its base 114 is the same as the width of region 11. Also, second region 13 further differs from first region 11 in that the cross-sectional area of second region 13 decreases as one moves from one end of region 13 to the other, i.e. second region 13 has a non-constant or decreasing cross-sectional dimension as one moves away from the end adjacent to region 11 towards first end 12. to second region 13 is third region 15. Third region 15 is generally longer than second region 13, usually at least about 4 fold longer and more usually at least about 5 fold longer. As such, the length 106 of third region 15 will generally range from about 5 mm to 15 mm, usually from about 7.5 mm to 12 mm and more usually from about 8.0 mm to 10.0 mm. The width of region 15 at its base 116, i.e. at the point most distal from first end 12, ranges from about 0.2 mm to 1.0 mm, usually from about 0.3 mm to 0.8 mm and more usually from about 0.4 mm to 0.6 mm. As with region 13, the cross-sectional area of region 15 may decrease as one moves towards first end 12. The rate of decrease is substantially less than the rate of decrease of region 13. As such, the rate of decrease is typically at least about 2 fold.

At second end 14 of device 10 is means 18 for attaching to an automated movement means, e.g. a movement arm of an automated device. The precise configuration of attachment means 18 will necessarily vary considerably depending on the automated device with which the applicator device is to be used. As such, the attachments means 18 may be sufficient for attaching to the movement arm of a number of different commercially available devices, where such devices include: the Biomek™ series of devices (Beckman Instruments), Bio-Grid™ and Micro-Grid™ (BioRobotics); Flexys™ (Genomic Solutions); Q-Bot (Genetix); and the like. The particular configuration of the attachment means is readily selected by one of skill in the art in view of the particular automated device to be employed.

A critical feature of the subject applicator devices is the first end 12. First end 12 is shown in greater detail in FIGS. 2A and 2B. As shown in FIGS. 2A and 2B and described above, first end 12 has a substantially planar surface 22. Planar surface 22 generally has a curvilinear cross-sectional shape, and is preferably circular as shown in FIG. 2A. The diameter 122 of planar surface 22 generally ranges from about 0.1 to 2 mm, usually from about 0.15 to 1.0 mm and more usually from about 0.2 to 0.6 mm, such that the cross-sectional area of planar surface 22 ranges from about 0.007 to 3.0 mm$^2$, usually from about 0.015 to 0.75 mm$^2$ and more usually from about 0.03 to 0.3 mm$^2$.

Arising from planar surface 22 is conical protuberance 16. Conical protuberance extrusion, prominence) 16 has a width or diameter at its base which is substantially less than the diameter of the planar surface from which it arises, generally being at least 2 fold less, usually at least about 3 fold less and more usually at least about 5 fold less. As such, the diameter 124 typically ranges from about 0.05 to 1 mm, usually from about 0.05 to 0.3 mm and more usually from about 0.05 to 0.2 mm. The height (length) 126 of the protuberance will be sufficient to prevent direct contact of the surface 22 to the surface onto which fluid samples are being deposited but will not be so great that fluid being transported on surface 22 does not come into direct contact with the surface onto which the fluid is to be deposited. Furthermore, the dimensions of the protuberance are sufficient to produce a substantially uniform circular fluid spot on the surface of a substrate, typically being from about 0.05 to 1.0 mm, usually from about 0.05 to 0.5 mm and more usually from about 0.05 to 0.2 mm.

The applicator device of the subject invention may be fabricated from any convenient material, where the entire device may be fabricated from the same material or may be fabricated from a plurality of different materials, e.g. where region 11 is fabricated from a material different from region 15 or where one of the regions is fabricated from a first material and then coated with a second material. Materials from which the applicator device may be fabricated include: stainless steel or other metals/metal alloys, plastics, ceramics, glass, quartz, and the like. In one preferred embodiment, at least the outer surface of the device, except for the planar surface 22 and protuberance 16, are coated with a material that is wetting resistant, e.g. hydrophobic, such as Teflon, and the like. In such embodiments, the amount of fluid sample that adheres to the sides of the applicator, and is therefore wasted during array preparation, is minimized. Thus, in such embodiments, the entire device may be fabricated from a first, wettable material, e.g. stainless steel, and then the sides of the device can be coated with a non-wettable material, such as Teflon, leaving only the planar surface 22 and protuberance 16 wettable.

The applicator device may be fabricated using any convenient technique, where the specific technique employed will generally depend on a number of different factors, including: the specific material from which the device is fabricated; economic etc. As such, fabrication techniques of interest include: machining, injection molding, point welding, casting; etc.

Also provided is an automated apparatus for producing microarrays that includes the subject applicator device. Such automated devices are known to those of skill in the art. Generally, such devices include an automated movement means, e.g. arm, that is operationally moved through the direction of a control unit. In such automated devices of the subject invention, one or more, usually a plurality of the subject applicator devices, is attached to the control arm. Commercially available devices with which the subject applicator may be employed include: Biomek 2000, Bio-Grid, Micro-Grid, Flexys, Q-bot, and the like.

METHODS OF USING THE APPLICATOR DEVICE

The applicator devices of the subject invention find use in depositing fluid samples onto the surface of a solid support, where the devices are capable of reproducibly depositing a fluid sample as a substantially uniform circular spot, where the spot will generally have a diameter ranging from about 0.1 to 2.0, usually from about 0.15 to 1.0 and more usually from about 0.2 to 0.6 mm. In depositing a fluid sample on a substrate surface with the subject applicator devices, the first step is to dip (i.e. introduce and retrieve; place in and then remove) the first end of the device into a fluid in a manner sufficient such that a volume of the fluid adheres to the first end of the device. The volume of fluid that adheres to the first end of the device should be sufficient to produce the desired spot, and will generally range from about 2 to 500 nl, usually from about 5 to 200 nl and more usually from about 5 to 50 nl.

The next step is to contact the first end of the device with the substrate surface in a manner sufficient such that at least a portion of the adhered fluid is deposited onto the substrate surface, where the portion that is deposited will be at least about 30%, usually at least about 40%, and may be as high as 70% of the fluid initially present on the first end of the device, such that the volume of fluid that is deposited will range from about 0.7 to 350 nl, usually from about 2.0 to 150 nl and more usually from about 2.0 to 35 nl. Sufficient contact is generally achieved by merely placing the tip of the conical protuberance onto the surface and holding the tip in place for a short period of time, where the period of time is generally at least about 0.5 s, usually at least about 1.0 s and may be as long as 5.0 s but will usually not exceed about 10.0 s. Following contact, the applicator device is removed, leaving the deposited spot on the surface of the substrate. The process is further illustrated in FIGS. 4A to 4C. FIG. 4A shows the applicator with fluid just prior to deposition. FIG. 4B shows the applicator contacting the substrate surface during deposition. FIG. 4C shows the applicator pulling away from the substrate surface following fluid deposition.

The substrates onto which the fluid is deposited with the subject applicator device may be fabricated from a variety of materials, where the substrate may be flexible or rigid. For flexible substrates, materials of interest include: nylon, both modified and unmodified, nitrocellulose, polypropylene, and the like, where a nylon membrane, as well as derivatives thereof, is of particular interest in this embodiment. For rigid substrates, specific materials of interest include: glass; plastics, e.g. polytetrafluoroethylene, polypropylene, polystyrene, polycarbonate, and blends thereof, and the like; metals, e.g. gold, platinum, and the like; other materials, e.g. silicon, silicon monoxide, and the like; etc. The substrates may be fabricated from the same material, or be composites of a plurality of different materials. Furthermore, the substrate surface may be treated with an agent which imparts desirable properties to the substrate surface, e.g. charge, the presence of desired functional groups, etc., where such treatments are known to those of skill in the art.

UTILITY

The subject applicator devices find use in a variety of applications where one wishes to deposit a fluid sample onto a substrate surface. In particular, the subject invention finds use in the production of arrays of biopolymeric agents, such as nucleic acid arrays, protein arrays, etc. Where arrays of biopolymeric agents are produced, the fluid sample that is deposited onto the support surface is generally an aqueous sample (or aqueous organic blend) comprising a biopolymeric agent, where the biopolymeric agent may be: a nucleic acid, e.g. oligonucleotide, polynucleotide; a peptide, e.g. poly peptide, protein; or other biopolymeric agent. As such, the subject invention finds use in the production of a variety of different kinds of arrays, including nucleic acid arrays, protein arrays, and the like. Such arrays find use in a variety of different applications, including: life science research applications, e.g. gene expression analysis, gene sequencing, drug screening, toxicology testing, etc.; clinical applications, e.g. diagnostics, etc., and the like.

KITS

Also provided by the subject invention are kits that include the subject applicator device. Kits of the subject invention at least include an applicator device having a conical protuberance at a first end and instructions on how to use the device to deposit a fluid sample (e.g. to produce an array of spots), on the surface of a substrate, where the instructions may be included in the kit as a package insert and or present on the packaging of the kit. The kit may further include one or more additional components, depending on the purpose for which the kit is designed. For example, the kit may further include a substrate and reagents necessary to produce a plurality of different biopolymeric fluid samples for deposition on the substrate surface. In addition, the kits may also comprise other mechanical components necessary to make arrays, such as a means for assembling an array of applicators that can simultaneously deposit fluid samples on a substrate surface.

It is evident from the above discussion that the subject invention provides for the production of improved biopolymeric arrays. The particular design of the subject invention provides for the deposition of fluid spots which are substantially uniform and circular in shape. Furthermore, the subject devices are able to produce the spots in a reproducible fashion. As such, the subject invention provides for a significant improvement over the current array production technology.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An applicator device for depositing a fluid sample onto the surface of a substrate, said device comprising:
   an elongate member with a first end and a second end, wherein said first end is characterized by the presence of a substantially planar surface having a diameter ranging from about 0.1 mm to 2.0 mm and a solid conical protuberance arising therefrom having a height that ranges from about 0.05 to about 0.2 mm and a diameter that is at least 5 fold less than the diameter of said substantially planar surface.

2. The applicator device according to claim 1, wherein said device has dimensions such that it is capable of depositing said fluid sample as a substantially uniform circular spot on said surface.

3. The applicator device according to claim 1, wherein said planar surface of said first end has a circular shape.

4. The applicator device according to claim 1, wherein said second end is characterized by the presence of a means for attaching to an automated movement means.

5. The applicator device according to claim 1, wherein said elongate member comprises three different regions of different dimensions between said first and second ends.

6. An applicator device for depositing a fluid sample in a substantially uniform circular spot on the surface of a substrate, said device comprising:
   an elongate member with a first end and a second end separated by three different regions of different dimensions, wherein said first end is characterized by the presence of a substantially circular planar surface having a diameter ranging from about 0.1 mm to 2.0 mm and a solid conical protuberance arising therefrom having a height that ranges from about 0.05 to about 0.2 mm and a diameter that is at least 5 fold less than the diameter of said substantially circular planar surface and said second end is characterized by the presence of a means for attaching to an automated movement means.

7. The device according to claim 6, wherein a first of said three different regions has a tubular shape with a constant cross-sectional dimension.

8. The device according to claim 6, wherein a second of said three different regions has a shape in which the cross-sectional dimension decreases from one end to the other at a first rate.

9. The device according to claim 8, wherein a third of said three different regions has a shape in which the cross-sectional dimension decreases from one end to the other at second rate that is less than said first rate.

10. An applicator device for depositing a fluid sample in a substantially uniform circular spot on the surface of a substrate, said device comprising:

an elongate member with a first end having a circular planar surface of a diameter ranging from about 0.1 to 2.0 mm and a solid conical protuberance having a height that ranges from about 0.05 to about 0.2 mm arising therefrom and a diameter that is at least 5 fold less than the diameter of said circular planar surface;

a first region of decreasing cross-sectional dimension;

a second region of decreasing cross-sectional dimension adjacent to said first region;

a third region of constant cross-sectional dimension adjacent to said second region; and a second end characterized by the presence of a means for attaching to an automated movement means.

11. A method of depositing a fluid sample on a substrate surface, said method comprising:

(a) contacting said first end of an applicator device according to claim 1 with said fluid sample in a manner sufficient for a volume of said sample to adhere to said first end; and (b) contacting said first end with said substrate surface in a manner sufficient to deposit said fluid sample on said surface.

12. The method according to claim 11, wherein said fluid sample comprises a biopolymer.

13. The method according to claim 12, wherein said biopolymer is selected from the group consisting of polypeptides and polynucleotides.

14. The method according to claim 12, wherein said fluid is positioned on said surface by placing the tip of said conical protuberance onto said surface to produce a biopolymeric array.

* * * * *